(12) United States Patent
Reed et al.

(10) Patent No.: US 6,280,730 B1
(45) Date of Patent: *Aug. 28, 2001

(54) ANTIBODIES THAT BIND TO α2-ANTIPLASMIN CROSSLINKED TO FIBRIN WHICH DO NOT INHIBIT PLASMA α2-ANTIPLASMIN

(75) Inventors: Guy L. Reed, Winchester, MA (US); Edgar Haber, Salisbury, NH (US); Gary R. Matsueda, Princeton, NJ (US)

(73) Assignee: The General Hospital Corporation, Boston, MA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/977,680

(22) Filed: Nov. 24, 1997

Related U.S. Application Data

(60) Continuation of application No. 08/680,634, filed on Jul. 16, 1996, now Pat. No. 5,831,031, which is a division of application No. 07/980,520, filed on Dec. 1, 1992, now Pat. No. 5,582,862, which is a continuation-in-part of application No. 07/943,372, filed on Sep. 10, 1992, now Pat. No. 5,372,812, which is a continuation of application No. 07/589,003, filed on Sep. 27, 1990, now abandoned, which is a continuation-in-part of application No. 07/177,222, filed on Apr. 4, 1988, now abandoned.

(51) Int. Cl.$^7$ .................. A61K 39/395; G01N 33/53; C07K 16/00; C12P 21/08
(52) U.S. Cl. .................. 424/141.1; 424/145.1; 424/158.1; 435/975; 530/387.1; 530/388.1; 530/388.25
(58) Field of Search .............. 530/388.1, 388.25, 530/387.1; 424/141.1, 145.1, 158.1; 435/975

(56) References Cited

U.S. PATENT DOCUMENTS

| | | |
|---|---|---|
| 4,147,765 | 4/1979 | Stephan et al. . |
| 4,198,335 | 4/1980 | Collen . |
| 4,245,040 | 1/1981 | Pilgeram . |
| 4,273,873 | 6/1981 | Sugitachi et al. . |
| 4,346,029 | 8/1982 | Collen . |
| 4,368,149 | 1/1983 | Masuho et al. . |
| 4,414,148 | 11/1983 | Jansen et al. . |
| 4,421,735 | 12/1983 | Haber et al. . |
| 4,455,290 | 6/1984 | Olexa et al. . |
| 4,470,925 | 9/1984 | Auditore-Hargreaves . |
| 4,474,893 | 10/1984 | Reading . |
| 4,545,988 | 10/1985 | Nakayama et al. . |
| 4,671,958 | 6/1987 | Rodwell et al. . |
| 4,673,573 | 6/1987 | Ferres et al. . |
| 4,722,903 | 2/1988 | Kudryk et al. . |
| 4,758,524 | 7/1988 | Bundesen et al. . |
| 4,833,085 | 5/1989 | Schaumann et al. . |
| 4,916,070 | 4/1990 | Matsueda et al. . |
| 4,927,916 | 5/1990 | Matsueda et al. . |
| 5,116,613 | 5/1992 | Haber et al. . |
| 5,372,812 | 12/1994 | Reed et al. . |
| 5,582,862 | 12/1996 | Reed et al. . |

FOREIGN PATENT DOCUMENTS

| | | |
|---|---|---|
| A-25387/84 | 9/1984 | (AU) . |
| 34872-A | 3/1985 | (AU) . |
| 063 002 A2 | 10/1982 | (EP) . |
| 0 088 994 A2 | 9/1983 | (EP) . |
| 0 120 694 A2 | 10/1984 | (EP) . |
| 0 125 023 A1 | 11/1984 | (EP) . |
| 0 142 905 A2 | 5/1985 | (EP) . |
| 0 146 050 A3 | 6/1985 | (EP) . |
| 0 159 025 A2 | 10/1985 | (EP) . |
| 0 187 658 A2 | 7/1986 | (EP) . |
| 0 271 227 A2 | 6/1988 | (EP) . |
| 61-268630 | 11/1986 | (JP) . |
| WO 83/03678 | 10/1983 | (WO) . |
| WO 83/03679 | 10/1983 | (WO) . |
| WO 83/03971 | 11/1983 | (WO) . |
| WO 85/00974 | 3/1985 | (WO) . |
| WO 86/01533 | 3/1986 | (WO) . |
| WO 87/05934 | 10/1987 | (WO) . |
| WO 87/06263 | 10/1987 | (WO) . |
| WO 87/06836 | 11/1987 | (WO) . |
| WO 88/03559 | 5/1988 | (WO) . |
| WO 89/09817 | 10/1989 | (WO) . |

OTHER PUBLICATIONS

European Search Report for EP 0 271 227 (Appl. No. 87310006.9) published Sep. 1989.

International Search Report for WO 88/03559 (Appl. No. PCT/US87/02968) published May 1988.

International Search Report for WO 89/09817 (Appl. No. PCT/US89/01065) published Oct. 1989.

International Search report for WO 87/06240 (Appl. No. PCT/US87/00860) published Oct. 1987.

Agnelli, G. et al., "The Comparative Effects of Recombinant Hirudin (CGP 39393) and Standard Heparin on Thrombus Growth in Rabbits," *Thrombosis and Hemostasis* 63(2):204–207 (1990).

(List continued on next page.)

*Primary Examiner*—Mark Navarro
(74) *Attorney, Agent, or Firm*—Sterne, Kessler, Goldstein & Fox P.L.L.C.

(57) ABSTRACT

The present invention relates to a treatment for myocardial infarction and blood clots within a patient, and more specifically to a therapy which enhances clot lysis comprising administering to a patient an antibody directed to α2-antiplasmin crosslinked to fibrin (α2AP-FX) which does not inhibit plasma α2-antiplasmin (α2AP). The invention also relates to a treatment for enhancing clot lysis comprising administering an antibody directed toward α2-antiplasmin crosslinked to fibrin which does not inhibit plasma α2AP together with a thrombolytic agent.

10 Claims, 4 Drawing Sheets

OTHER PUBLICATIONS

Agnelli, G. et al., "A Comparison of the Thrombolytic and Hemorrhagic Effects of Tissue–type Plasminogen Activator and Streptokinase in Rabbits," *Circulation* 72(1):178–182 (1985).

Agnelli, B. et al., "Sustained Thrombolysis With DNA–Recombinant Tissue Type Plasminogen Activator in Rabbits," *Blood* 66(2):399–401 (Aug. 1985).

Angles–Cano, E. R., "Tissue Plasminogen Activator Determination With a Fibrin–supported Film," *Chem. Abstracts* 104:307–308, Abstract No. 144639d (1986).

Aoki, N. et al., "Fibrin–Associated Plasminogen Activation in $\alpha_2$–Plasmin Inhibitor Deficiency," *Blood* 62(5):1118–1122 (Nov. 1983).

Bates, E. R. et al.,"A Monoclonal Antibody Against the Platelet Glycoprotein IIb/IIIa Receptor Complex Prevents Platelet Aggregation and Thrombosis in a Canine Model of Coronary Angioplasty," *Circulation* 84(6):2463–2469 (Dec. 1991).

Bode, C. et al., "Conjugation to Antifibrin Fab'Enhances Fibrinolytic Potency of Single–Chain Urokinase Plasminogen Activator," *Circulation* 81(6):1974–1980 (Jun. 1990).

Bode, C. et al., "Antibody–Directed Urokinase: A Specific Fibrinolytic Agent," *Science* 229:765–767 (Aug. 1985).

Bode, C. et al., "Thrombolysis by a Fibrin–specific Antibody Fab'–Urokinase Conjugate," *J. Mol. Cell. Cardiol.* 19:335–341 (Apr. 1987).

Bode, C. et al., "Antibody–directed Fibrinolysis: An Antibody Specific For Both Fibrin and Tissue Plasminogen Activators," *J. Biol. Chem.* 264(2):944–948 (Jan. 1989).

Boulianne, G. L. et al., "Production of Functional Chimaeric Mouse/Human Antibody," *Nature* 312:643–646 (Dec. 1984).

Branscomb, E. E. et al., "Bispecific Monoclonal Antibodies Produced by Somatic Cell Fusion Increase the Potency of Tissue Plasminogen Activator," *Thrombosis and Haemostasis* 64(2):260–266 (1990).

Brennan, M. et al., "Preparation of Bispecific Antibodies by Chemical Recombination of Monoclonal Immunoglobulin $G_1$ Fragments," *Science* 229:81–83 (Jul. 1985).

Carrasquillo, J. A. et al., "Radioimmunodetection of Human Melanoma with Monoclonal Antibodies and Fab Fragments," in: *Radioimmunoimaging and Radioimmunotherapy*, Burchiel, S. and B. Rhodes, Eds, Elsevier Science Publishing Co., Inc.; Amsterdam, pp. 357–368 (1983).

Charpie, J. R. et al., "A Bispecific Antibody Enhances the Fibrinolytic Potency of Single–Chain Urokinase," *Biochemistry* 29(27):6374–6378 (1990).

Collen, D. et al., "Thrombolysis with Human Extrinsic (Tissue–Type) Plasminogen Activator in Rabbits with Experimental Jugular Vein Thrombosis," *J. Clin. Invest.* 71:368–376 (Feb. 1983).

Collen, D. et al., "Thrombolytic and Pharmacokinetic Properties of Chimeric Tissue–Type and Urokinase–Type Plasminogen Activators," *Circulation* 84(3):1216–1234 (Sep. 1991).

Collen, D. et al., "Synergism of Thrombolytic Agents in vivo," *Circulation* 74(4):838–842 (Oct. 1986).

DeWood, M. A. et al., "Prevalence of Total Coronary Occlusion During the Early Hours of Transmural Myocardial Infarction," *New England J. Med.* 303(16):897–902 (Oct. 1980).

Dorai, H. and G. P. Moore, "The Effect of Dihydrofolate Reductase–Mediated Gene Amplification on the Expression of Transfected Immunoglobulin Genes," *J. Immunol.* 139(12):4232–4241 (Dec. 1987).

Duberstein, R., "Scientists Develop New Technique for Producing Bispecific Monoclonals," *Genetic Engineering News* 6:22–24 (1986).

Emeis, J. J. and J. H. Verheijen, "Thrombolytic Properties in a Rabbit Jugular Vein Thrombosis Model of a Tissue–type Plasminogen Activator Mutant Lacking the Growth Factor– and Kringle One–Domains," *Arzneim.–Forsch./Drug Res.* 42(3):358–362 (1992).

Fisher, R. et al., "Isolation and Characterization of the Human Tissue–type Plasminogen Activator Structural Gene Including Its 5' Flanking Region," *J. Biol. Chem.* 260(20):11223–11230 (Sep. 1985).

Gardell, S. J. et al., "Effective Thrombolysis Without Marked Plasminemia After Bolus Intravenous Administration of Vampire Bat Salivary Plasminogen Activator in Rabbits," *Circulation* 84(1):244–253 (Jul. 1991).

Gold, H. K. et al., "Acute Coronary Reocclusion After Thrombolysis With Recombinant Human Tissue–type Plasminogen Activator: Prevention by a Maintenance Infusion," *Circulation* 73(2):347–352 (Feb. 1986).

Haber, E. et al., "Antibody Targeting as a Thrombolytic Strategy," *Annals N. Y. Acad. Sci.* 667:365–381 (Dec., 1992).

Harris, W. J. and S. Emery, "Therapeutic Antibodies—The Coming of Age," *T. Biotech.* 111:42–44 (1993).

Hattey, E. et al., "Monoclonal Antibodies Against Plasminogen and Alpha–2–Antiplasmin: Binding to Native and Modified Antigens," *Thrombosis Res.* 45:485–495 (Mar. 1987).

Hessel, B. et al., "Primary Structure of Human Fibrinogen and Fibrin: Structural Studies on $NH_2$–terminal Part of Bβ Chain," *Eur. J. Biochem.* 98:521–534 (1979).

Houranieh, A. et al., "Monoclonal Antibodies to Human Cross–Linked Fibrin," *Fed. Proc.* 44:1846, Abstract No. 8381 (Mar. 1985).

Hui, K. Y. et al., "Immunodetection of Human Fibrin Using Monoclonal Antibody–64C5 in an Extracorporeal Chicken Model," *Thrombosis and Haemostasis* 54(2):524–527 (1985).

Hui, K. Y. et al., "Monoclonal Antibodies of Predetermined Specificity for Fibrin: A Rational Approach to Monoclonal Antibody Research," *Hybridoma* 5(3):215–222 (1986).

Hui, K. Y. et al., "Monoclonal Antibodies to a Synthetic Fibrin–Like Peptide Bind to Human Fibrin but not Fibrinogen," *Science* 222:1129–1132 (Dec. 1983).

Ito, R. K. et al., "Fibrinolysis Studies: Fibrinogen–Specific Antibody as Carriers for Fibrinolytic Agents," *Fed. Proc.* 44:1846, Abstract No. 8283 (1985).

Kabnick, K. S. and D. E. Housman, "Determinants That Contribute to Cytoplasmic Stability of Human c–fos and β–Globin mRNAs Are Located at Several Sites in Each mRNA," *Mol. Cell. Biol.* 8(8):3244–3250 (Aug. 1988).

Kato, K. et al., "A Specific Immunoassay System for Hybrid Type Antigens," *Chem. Abstracts* 94:325, Abstract No. 61048j (Mar. 1981).

Kimura, S. et al., "Acceleration of Fibrinolysis by the N–Terminal Peptide of $\alpha_2$–Plasmin Inhibitor," *Blood* 66(1):157–160 (Jul. 1985).

Kudryk, B. et al., "A Monoclonal Antibody With Ability to Distinguish Between NH$_2$–Terminal Fragments Derived From Fibrinogen and Fibrin," *Mol. Immunol.* 20(11):1191–1200 (1983).

Kudryk, B. et al., "Specificity of a Monoclonal Antibody for the NH$_2$–Terminal Region of Fibrin," *Mol. Immunol.* 21(1):89–94 (1984).

Kumada, T. and Y. Abiko, "Physiological Role of $\alpha_2$–Plasmin Inhibitor in Rats," *Thrombosis Res.* 36:153–163 (1984).

Laffel, G. L. and E. Braunwald, "Thrombolytic Therapy: A New Strategy for the Treatment of Acute Myocardial Infarction (First of Two Parts)," *New England J. Med.* 311(11):710–717 (Sep. 1984).

Laffel, G. L. and E. Braunwald, "Thrombolytic Therapy: A New Strategy for the Treatment of Acute Myocardial Infarction (Second of Two Parts)," *New England J. Med.* 311(12):770–776 (Sep. 1984).

Lanzavecchia, A. and D. Scheidegger, "The Use of Hybrid Hybridomas to Target Human Cytotoxic T Lymphocytes," *Eur. J. Immunol.* 17:105–111 (Jan. 1987).

Larsen, G. R. et al., "Protein Engineering of Novel Plasminogen Activators with Increased Thrombolytic Potency in Rabbits Relative to Activase," *J. Biol. Chem.* 266(13):8156–8161 (May 1991).

Lawn, R. M. et al., "The Nucleotide Sequence of the Human β–Globin Gene," *Cell* 21:647–651 (Oct. 1980).

Lijnen, H. R. et al., "Comparative Fibrinolytic Properties of Staphylokinase and Streptokinase in Animal Models of Venous Thrombosis," *Thrombosis and Haemostasis* 66(4):468–473 (1991).

Lijnen, H. R. et al., "Biochemical and Thrombolytic Properties of a Low Molecular Weight Form (Comprising Leu$^{144}$ through Leu$^{411}$) of Recombinant Single–chain Urokinase–type Plasminogen Activator," *J. Biol. Chem.* 263(12):5594–5598 (Apr. 1988).

Liu, M. A. et al., "Heteroantibody Duplexes Target Cells For Lysis by Cytotoxic T Lymphocytes," *Proc. Natl. Acad. Sci. USA* 82:8648–8652 (Dec. 1985).

Love, T. W. et al., "Recombinant Antibodies Possessing Novel Effector Functions," *Meth. Enzymol.* 178:515–527 (1989).

Lukacova, D. et al., "Inhibition of Factor XIII Activation by an Anti–Peptide Monoclonal Antibody," *Biochemistry* 30(42):10164–10170 (1991).

Martin, U. et al., "Properties of a Novel Plasminogen Ativator (BM 06.022) produced in *Escherichia coli*," *Z. Kardiol.* 79(Suppl. 3):167–170 (1990).

Matsueda, G. R. et al., "A Monoclonal Antibody Specific for the C Terminus of Fibrinogen and Fibrin Gamma Chains," *FASEB J.* 2(5):A1411, Abstract No. 6480 (Mar. 1988).

Matsueda, G. R. et al., "Fibrin–Specific Monoclonal Antibodies are Elicited by Immunization with a Synthetic Fibrin–Like Peptide," *Fibrinogen:Structural Variants and Interactions*, vol. 3, Henschen, A. et al., Eds., Walter de Gruyter, Berlin, (1985).

Matsueda, G. R. et al., "Monoclonal Antibodies Specific for Human Fibrin Monomer," *Fed. Proc.* 42(7):1992, Abstract No. 1375 (May 1983).

Matsueda, G. R. et al., "Detection of Thrombi: A Chicken Model Using Monoclonal Antibody Which Binds to Human Fibrin but not Fibrinogen," *Haemostasis* 14(1):44, Abstract No. 75 (Mar. 1984).

Matsueda, G. R. et al., "Synthetic Fibrin–Like Peptides Used as Antigens Yield Fibrin–Specific Antibodies," *Peptides: Structure and Function. Proceedings of the Eighth American Peptide Symposium*, Hruby, V. J. and D. H. Rich, Eds., Pierce Chemical Company, Rockford, IL pp. 873–876 (1983).

Matsuo, O. et al., "Thrombolytic Effects of Single–Chain Pro–Urokinase in a Rabbit Jugular Vein Thrombosis Model," *Thrombosis Res.* 42:187–194 (1986).

Matsuo, O. et al., "Comparison of the Relative Fibrinogenolytic, Fibrinolytic and Thrombolytic Properties of Tissue Plasminogen Activator and Urokinase in Vitro," *Thrombos. Haemostas.* 45(3):225–229 (1981).

McCabe, R. P. et al., "A Diagnostic–Prognostic Test for Bladder Cancer Using a Monoclonal Antibody–based Enzyme–linked Immunoassay for Detection of Urinary Fibrin(ogen) Degradation Products," *Cancer Res.* 44:5886–5893 (Dec. 1984).

Miles, L. A. et al., "A Bleeding Disorder Due to Deficiency of $\alpha_2$–Antiplasmin," *Blood* 59(6):1246–1251 (Jun. 1982).

Milstein, C. and A. C. Cuello, "Hybrid Hybridomas and their Use in Immunohistochemistry," *Nature* 305:537–540 (Oct. 1983).

Mimuro, J. et al., "Monoclonal Antibodies to Discrete Regions in $\alpha_2$–Plasmin Inhibitor," *Blood* 69(2):446–453 (Feb., 1987).

Morrison, S. L. and V. T. Oi, "Genetically Engineered Antibody Molecules," *Adv. Immunol.* 44:65–92 (1989).

Morrison, S. L., "Transfectomas Provide Novel Chimeric Antibodies," *Science* 229:1202–1207 (Sep. 1985).

Morrison, S. L. et al., "Chimeric Human Antibody Molecules: Mouse Antigen–binding Domains with Human Constant Region Domains," *Proc. Natl. Acad. Sci. USA* 81:6851–6855 (Nov. 1984).

Munro, A., "Uses of Chimaeric antibodies," *Nature* 312:597 (Dec. 1984).

Neuberger, M. S. et al., "Recombinant Antibodies Possessing Novel Effector Functions," *Nature* 312:604–608 (Dec. 1984).

Neuberger, M. S. et al., "A Hapten–specific Chimaeric IgE Antibody with Human Pysiological Effector Fuctions," *Nature* 314:268–270 (Mar. 1985).

Nisonoff, A. and W. J. Mandy, "Quantitative Estimation of the Hybridization of Rabbit Antibodies," *Nature* 194:355–359 (Apr. 1962).

Nossel, H. L., "Relative Proteolysis of the Fibrinogen Bβ Chain By Thrombin and Plasmin as a Determinant of Thrombosis," *Nature* 291:165–167 (May 1981).

Oi, V. T. and S. L. Morrison, "Chimeric Antibodies," *BioTechniques* 4(3):214–221 (1986).

Pacella, B. L. et al., "Induction of Fibrin–Specific Antibodies by Immunization with Synthetic Peptides That Correspond to Amino Termini of Thrombin Cleavage Sites," *Mol. Immunol.* 20(5):521–527 (1983).

Philpott, G. W. et al., "Selective Cytotoxicity of Hapten–Substituted Cells With an Antibody–Enzyme Conjugate," *J. Immunol.* 111(3):921–929 (Sep. 1973).

Philpott, G. W. et al., "Selective Binding and Cytotoxicity of Rat Basophilic Leukemia Cells (RBL–1) with Immunoglobulin E–Biotin and Avidin–Glucose Oxidase Conjugates," *J. Immunol.* 125(3):1201–1209 (Sep. 1980).

Pizzo, S. V. et al., "The Effect of Plasmin on the Subunit Structure of Human Fibrin," *J. Biol. Chem.* 248(13):4574–4583 (Jul. 1973).

Plow, E. F. et al., "Changes in Antigenic Structure and Conformation of $\alpha_2$–Antiplasmin Induced by Interaction with Plasmin," *J. Biol. Chem.* 255(7):2902–2906 (Apr. 1980).

Rajagopalan, S. et al., "A Nonantigenic Covalent Streptokinase–Polyethylene Glycol Complex with Plasminogen Activator Function," *J. Clin. Invest.* 75:413–419 (Feb. 1985).

Reed, G. L. et al., "Inhibiton of Clot–Bound $\alpha_2$–Antiplasmin Enhances In Vivo Thrombolysis," *Circulation* 82(1):164–168 (Jul. 1990).

Reed, G. L. et al., "Acceleration of Plasma Clot Lysis by an Antibody to $\alpha_2$–Antiplasmin," *Trans. Assoc. Am. Phys.* 101:250–256 (1988).

Reed, G. L. et al., "Synergistic Fibrinolysis: Combined Effects of Plasminogen Activators and an Antibody That Inhibits $\alpha_2$–antiplasmin," *Proc. Natl. Acad. Sci. USA* 87(3):1114–1118 (Feb. 1990).

Reed, G. L. et al., "Selective Inhibition of $\alpha_2$–Antiplasmin Augments the Potency and Specificity of Plasminogen Activators," *J. Am. Coll. Cardiol.* 13(2):2A (Feb. 1989).

Rosebrough, S. F. et al., "Radioimmunoimaging of Venous Thrombi Using Iodine–131 Monoclonal Antibody," *Radiology* 156:515–517 (Aug. 1985).

Runge, M. S. et al., "Antibody–Enhanced Thrombolysis: Capture of Tissue Plasminogen Activator by a Bispecific Antibody and Direct Targeting by an Antifibrin–Tissue Plasminogen Activator Conjugate In Vivo," *Trans. Assoc. Am. Phys.* 100:250–255 (May 1987).

Runge, M. S. et al., "Conjugate to an Antifibrin Monoclonal Antibody Enhances the Fibrinolytic Potency of Tissue Plasminogen Activator in Vitro," *Biochemistry* 27:1153–1157 (1988).

Runge, M. S. et al., "Increasing Selectivity of Plasminogen Activators with Antibodies," *Clin. Res.* 36(5):501–506 (Sep. 1988).

Runge, M. S. et al., "Antibody–enhanced Thrombolysis: Targeting of Tissue Plasminogen Activator in vivo," *Proc. Natl. Acad. Sci. USA* 84:7659–7662 (Nov. 1987).

Runge, M. S. et al., "Antibody–Directed Fibrinolysis: A Bispecific (Fab')$_2$ That Binds to Fibrin and Tissue Plasminogen Activator," *Bioconjugate Chemistry* 1(4):274–277 (1990).

Sakata, Y. and N. Aoki, "Significance of Cross–Linking of a $\alpha_2$–Plasmin Inhibitor to Fibrin in Inhibition of Fibrinolysis and in Hemostasis," *J. Clin. Invest.* 69:536–542 (Mar. 1982).

Scheefers–Borchel, U. et al., "Discrimination Between Fibrin and Fibrinogen by a Monoclonal Antibody Against a Synthetic Peptide," *Proc. Natl. Acad. Sci. USA* 82:7091–7095 (Oct. 1985).

Schnee, J. M. et al., "Construction and Expression of a Recombinant Antibody–targeted Plasminogen Activator," *Proc. Natl. Acad. Sci. USA* 84:6904–6908 (Oct. 1987).

Sevilla, C. L. et al., "Plasminogen Activator–Anti–Human Fibrinogen Conjugate," *Fed. Proc.* 44(4):1073, Abstract No. 3872 (Mar. 1985).

Sevilla, C. L. et al., "Plasminogen Activator–Anti–Human Fibrinogen Conjugate," *Biochem. Biophys. Res. Commun.* 130(1):91–96 (Jul. 1985).

Sharma, G. V. R. K. et al., "Medical Intelligence: Thrombolytic Therapy," *N. England. J. Med.* 306(21):1268–1276 (May 1982).

Sharon, J. et al., "Expression of a $V_H C_K$ chimaeric protein in mouse myeloma cells," *Nature* 309:364–367 (May 1984).

Sobel, B. E. et al., "Augmented and Sustained Plasma Concentrations After Intramuscular Injections of Molecular Variants and Deglycosylated Forms of Tissue–Type Plasminogen Activators," *Circulation* 81(4):1362–1373 (Apr. 1990).

Sobel, J. H. et al., "Characterization of a Crosslink–Containing Fragment Derived from the $\alpha$ Polymer of Human Fibrin and Its Application in Immunologic Studies using Monoclonal Antibodies," *Thrombos. and Haemostas.* 46(1):240, Abstract No. 0758 (Jul. 1981).

Soria, J. et al., "Monoclonal Antibodies that React Preferentially With Fibronigen Degradation Products or With Cross–Linked Fibrin Split Products," *Ann. N. Y. Acad. Sci* 408:665–666 (1983).

Staerz, U. D. and M. J. Bevan, "Hybrid Hybridoma Producing a Bispecific Monoclonal Antibody that Can Focus Effector T–cell Activity," *Proc. Natl. Acad. Sci. USA* 83:1453–1457 (Mar. 1986).

Stump, D. C. et al., "Comparative Thrombolytic Properties of Single–Chain Forms of Urokinase–Type Plasminogen Activator," *Blood* 69(2):592–596 (Feb. 1987).

Thorpe, R. et al., "Single Shot Intrasplenic Immunization: An Advantageous Procedure for Production of Monoclonal Antibodies Specific for Human Fibrin Fragments," *Hybridoma* 3(4):381–385 (1984).

Tucker, P. W. et al., "Sequence of the Cloned Gene for the Constant Region of Murine $\gamma$2b Immunoglobulin Heavy Chain," *Science* 206:1303–1306 (Dec. 1979).

van Zonneveld, A. et al., "Structure and Function of Human Tissue–Type Plasminogen Activator (t–PA)," *J. Cell. Biochem.* 32:169–178 (1986).

Verde, P. et al., "Identification and Primary Sequence of an Unspliced Human Urokinase Poly(A)$^+$ RNA," *Proc. Natl. Acad. Sci. USA* 81:4727–4731 (Aug. 1984).

Waldmann, T. A., "Monoclonal Antibodies in Diagnosis and Therapy," *Science* 252:1657–1662 (Jun. 1991).

Whitaker, A. N. et al., "Measurement of Crosslinked Fibrin Degradation Products Using Monoclonal Antibodies: Use in the Study of Intravascular Coagulation," *Pathology* 16:357–358 (Jul. 1984).

Williams, G. T. and M. S. Neuberger, "Production of Antibody–tagged Enzymes by Myeloma Cells: Application to DNA Polymerase I Klenow Fragment," *Gene* 43:319–324 (1986).

Wiman, B. et al., "Determination of Plasmin–$\alpha_2$–antiplasmin Complex in Plasma Samples by Means of a Radioimmunoassay," *Scand. J. Clin. Lab. Invest.* 43:27–33 (1983).

Wojta, J. et al., "Anwendung monoklonaler Antikörper in der Fibrinolysediagnostik," *Wiener klinische Wochenschrift* 97(5):244–248 (1985).

Zamarron, C. et al., "Influence of Exogenous and Endogenous Tissue–Type Plasminogen Activator on the Lysability of Clots in a Plasma Milieu In Vitro," *Thrombosis Res.* 35:335–345 (1984).

English language abstract of Japanese Patent No. 61–268630, WPI Acc. No. 87–010915/02.

English Language Translation of Wojta, J. et al. (Ref. No. AT36).

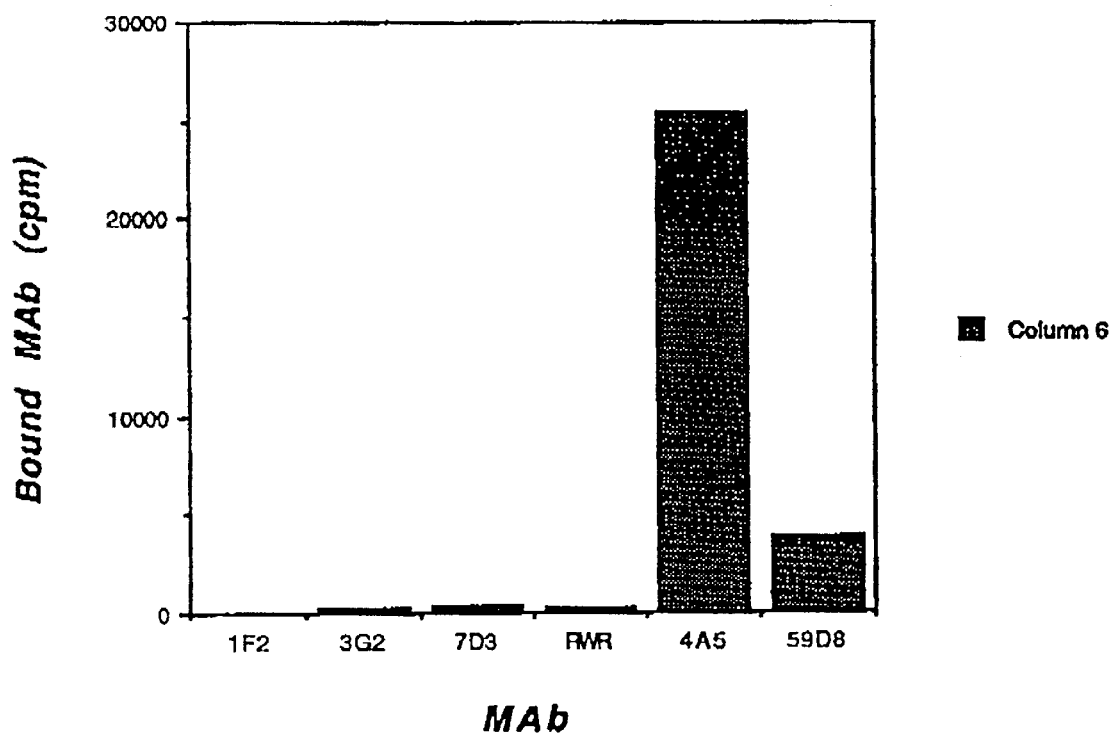
Fig. 2. Binding of a2AP-Fx MAbs to Fibrinogen

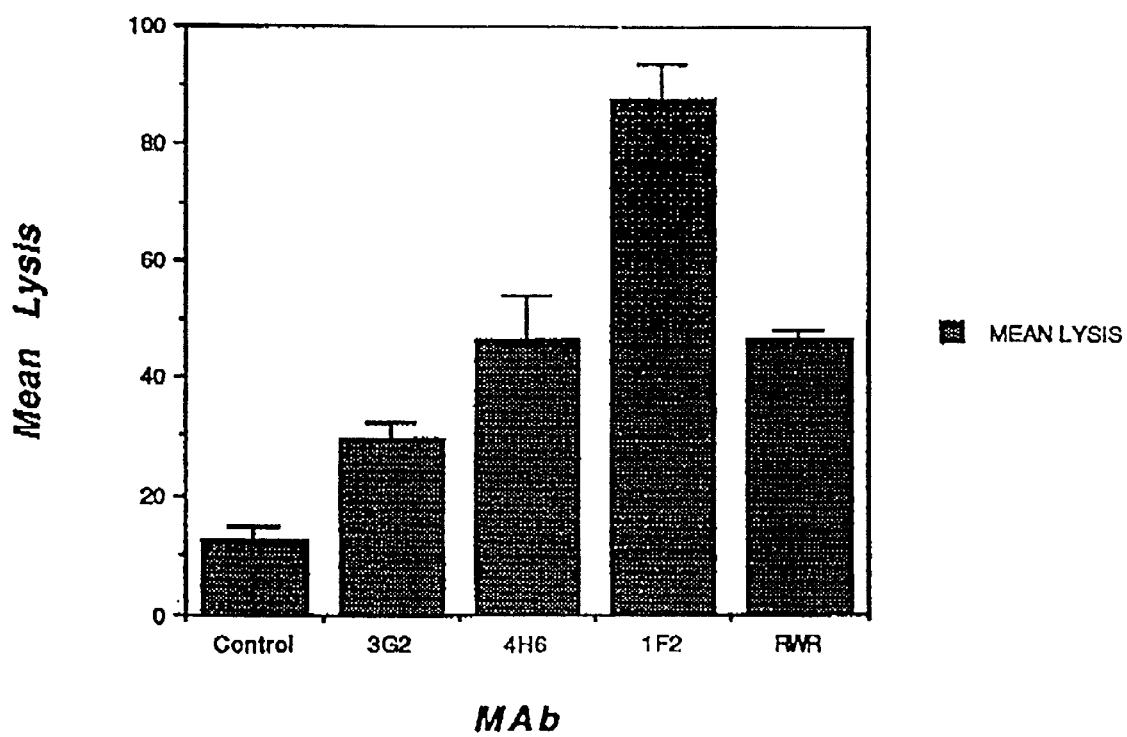
Fig. 3. Clot Lysis by a2AP-Fx MAbs

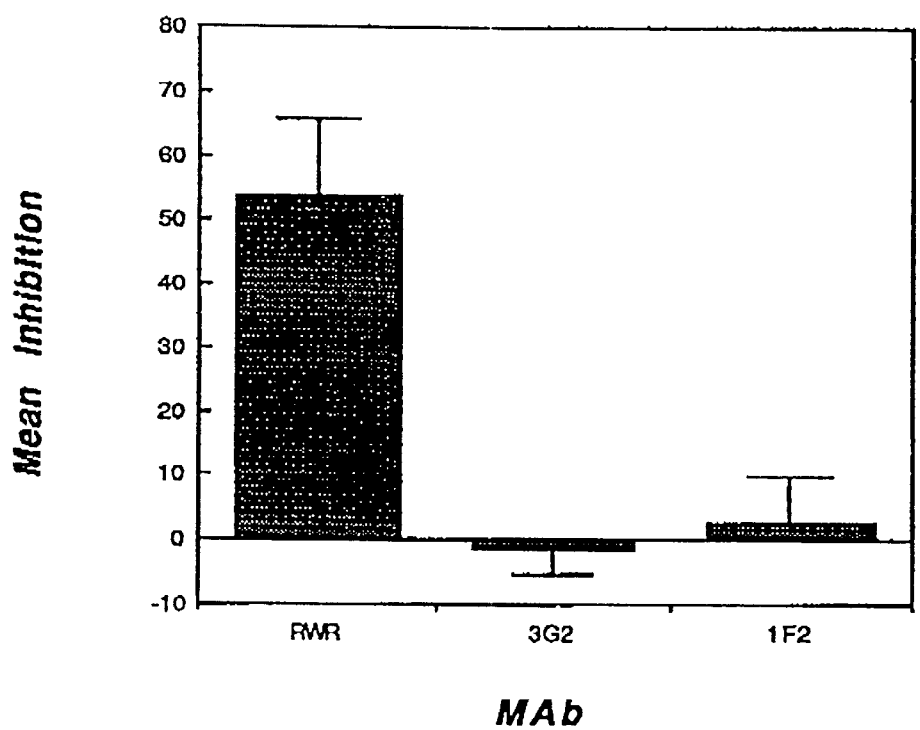
Fig. 4. Inhibition of Soluble a2AP by a2AP-Fx MAbs

ANTIBODIES THAT BIND TO α2-ANTIPLASMIN CROSSLINKED TO FIBRIN WHICH DO NOT INHIBIT PLASMA α2-ANTIPLASMIN

This application is a continuation of application Ser. No. 08/680,634, filed Jul. 16, 1996, now U.S. Pat. No. 5,831,031 which is a divisional of application Ser. No. 07/980,520, filed Dec. 1, 1992 (U.S. Pat. No. 5,582,862, issued Dec. 10, 1996), which is a continuation-in-part of application Ser. No. 07/943,372, filed Sep. 10, 1992 (U.S. Pat. No. 5,372,812, issued Dec. 13, 1994), which is a continuation of application Ser. No. 07/589,003, filed Sep. 27, 1990 (abandoned), which is a continuation-in-part of application Ser. No. 07/177,222, filed Apr. 4, 1988 (abandoned), the contents of which are incorporated herein by reference.

This invention was made with Government support under Contract #HL-02348 awarded by the National Institutes of Health. The Government has rights in this invention.

BACKGROUND OF THE INVENTION

FIELD OF THE INVENTION

The present invention relates to a treatment for myocardial infarction and blood clots within a patient, and more specifically to a therapy which enhances clot lysis comprising administering to a patient an antibody directed to α2-antiplasmin crosslinked to fibrin (α2AP-Fx) which does not inhibit plasma α2-antiplasmin (α2AP). The invention also relates to a treatment for enhancing clot lysis comprising administering an antibody directed toward α2-antiplasmin crosslinked to fibrin which does not inhibit plasma α2AP together with a thrombolytic agent.

BACKGROUND INFORMATION

The initiating event of many myocardial infarctions (heart attacks) is the hemorrhage into atherosclerotic plaque. Such hemorrhage often results in the formation of a thrombus (or blood clot) in the coronary artery which supplies the infarct zone (i.e., an area of coagulation necrosis which results from an obstruction of blood circulation). This thrombus is composed of a combination of fibrin and blood platelets. The formation of a fibrin-platelet clot has serious clinical ramifications. The degree and duration of the occlusion caused by the fibrin-platelet clot determines the mass of the infarct zone and the extent of damage.

A. Treatment for Myocardial Infarction

The primary goal of current treatment for myocardial infarction involves the rapid dissolution of the occluding thrombus and the restoration of blood flow ("reperfusion"). An agent which is capable of selectively binding to and affecting may enhance thrombolysis and may decrease the risk of general hemorrhage to the patient. A successful therapy must be capable of sustained effect so that reformation of the clot does not occur after the cessation of therapy. If the fibrin-platelet clot is able to reform, then the affected artery may become reoccluded.

The formation of fibrin-platelet clots in other parts of the circulatory system may be partially prevented through the use of anti-coagulants (such as heparin). Unfortunately, heparin has not been found to be universally effective in preventing reocclusion in myocardial infarction victims in which the degree of blood vessel occlusion (the degree of "stenosis") is greater than or equal to 70%, particularly in those patients with severe residual coronary stenosis.

If an individual has formed a fibrin-platelet clot prior to the availability of medical assistance, the clot may be dissolved through the use of thrombolytic agents. A thrombolytic agent is a medicament capable of lysing the fibrin-platelet thrombus, and thereby permitting blood to again flow through the affected blood vessel. Such agents include, but are not limited to, streptolinase, prourokinase, urokinase, staphylokinase and tissue-type plasminogen activator (Ganz, W. et al., *J. Amer. Coll. Cardiol.* 1:1247–1253 (1983); Rentrop, K. P. et al., *Amer. J. Cardiol.* 54:29E–31E (1984); Gold, H. K. et al., *Amer. J. Cardiol.* 53:122C–125C (1984)).

B. Mechanism of Fibrin Clot Formation

Clots are composed of both fibrin and blood platelets in various ratios. The fundamental reaction in blood clotting involves the conversion of a soluble plasma protein (fibrinogen) into insoluble fibrin. The conversion of fibrinogen into fibrin is catalyzed by the enzyme thrombin, which is a serine protease. Fibrin chains are crosslinked to each other by activated Factor XIII. Similarly activated Factor XIII crosslinks α2AP to fibrin, concentrating the inhibitor on the clot surface. These two crosslinking events render the fibrin clot highly resistant to lysis. The general mechanism of blood clot formation is reviewed by Ganong, W. F. (*In: Review of Medical Physiology*, 9th ed., Lange, Los Altos, Calif., pp. 411–414 (1979)). Platelets are disk-shaped structures present in blood. They contribute to clot formation by both their incorporation with fibrin into an insoluble mass and by their enhancement of the rate of fibrinogen to fibrin conversion and by providing Factor XIII to enhance fibrin/α2AP crosslinking. Platelets contribute to clot formation in myocardial infarction and are a major component of clots that reocclude coronary arteries that have been reperfused by treatment with a thrombolytic agent.

C. Mechanism of Clot Lysis and Natural Inhibition Thereof

Clot lysis is mediated by plasmin in vivo. Under natural conditions, plasminogen is converted to plasmin by tissue plasminogen activator (t-PA). Activation occurs on the fibrin surface, thus confining proteolytic activity to the appropriate site. After plasmin is set free into the circulation, it is rapidly combined with natural inhibitors. Inactivation of plasmin is the final and necessary step in the process of protecting against undesirable proteolysis. Such plasmin inhibitors include α2-antiplasmin, α2-macroglobulin and α1-antitrypsin, all glycoproteins. α2-antiplasmin has a much higher affinity for plasmin than α2-macroglobulin and binds specifically to plasmin in a 1:1 ratio. The larger pool of α-macroglobulin acts as a reservoir inhibitor. Kane, K. K., *Ann. Clin. Lab. Sci.* 14:443–449 (1984). Thus, clot lysis by the administration of plasminogen activators is limited by the rapid and irreversible inactivation of plasmin by plasmin inhibitors.

α2-antiplasmin has three functional domains: the reactive site for plasmin, the plasmin(ogen) or LBS-binding site [complementary to the LBS (lysine-binding site) of plasmin (ogen)], and the cross-linking site for fibrin. Mimuro, J. et al., *Blood* 69:446–453 (1987). Mimuro et al. disclose antibodies to α2-antiplasmin, one of which (JPTI-1) was specific to the reactive site of α2-antiplasmin and prevented formation of α2-antiplasmin-plasmin complexes, thereby inhibiting antiplasmin activity. However, Mimuro et al. do not teach administration of the JPTI-1 antibody to enhance clot lysis. Other antibodies specific for α2-antiplasmin are taught by Plow, E. F. et al., *J. Biol. Chem.* 255:2902–2906 (1980); Wimen, B. et al., *Scan. J. Clin. Lab. Invest.* 43:27–33 (1983); Hattey, E. et al., *Thromb. Res.* 45:485–495 (1987); Collen, U.S. Pat. No. 4,346,029 (1980); and Collen, U.S. Pat. No. 4,198,335 (1980).

D. α2-Antiplasmin Crosslinked to Fibrin

During clotting, α2AP is crosslinked to fibrin by Factor XIIIa. Aoki and colleagues have demonstrated that this crosslinking of α2AP to fibrin is important in preventing the "endogenous fibrinolysis" that occurs when fibrin-bound plasminogen is activated by fibrin-bound, endogenous, plasminogen activator (Aoki, N. et al., *Blood* 62:1118–1122 (1983)). This crosslinking may serve as a means of concentrating α2AP at the alpha chain site where fibrin appears particularly vulnerable to attack by plasmin (Pizzo, S. V. et al., *J. Biol. Chem.* 248:4574–4583 (1973)). Plasma clots deficient in crosslinked α2AP undergo a spontaneous lysis when suspended in buffer or plasma containing normal amounts of α2AP; the rate of lysis is proportional to the amount of α2AP incorporated into the clot (Sakata, Y. and Aoki, N., *J. Clin. Invest.* 69:536–542 (1982)). In a similar fashion, the crosslinking of α2AP to fibrin may be inhibited by a 0.13 mM concentration of a peptide that represents the 12 amino-terminal residues of α2AP (Kimura, S. et al., *Blood* 66:157–160 (1985)). This inhibition of crosslinking results in clots that lyse more readily upon exposure to fibrinolytic agents. In thrombolytic situations, fibrin-bound α2AP may be the most important inhibitor of clot lysis; whereas the chief role of soluble α2AP may be to prevent circulating plasmin from degrading other clotting factors.

Work with antibody RWR, has confirmed the importance of α2AP crosslinking in stabilizing the clot against lysis (Reed et al., *Proc. Natl. Acad. Sci. USA* 87:1114–1118 (1990), Reed et al., *Circulation* 82:164–168 (1990)). For example, in experiments using compressed and washed plasma clots (to clear away unbound α2AP), RWR alone causes the clots to undergo spontaneous lysis (Reed et al., *Proc. Natl. Acad. Sci. USA* 87:1114–1118 (1990). This spontaneous lysis is probably due to uninhibited plasmin generated by fibrin-associated t-PA's action on fibrin bound plasminogen as has been suggested for α2AP deficiency (Aoki, N. et al., *Blood* 62:1118–1122 (1983)). In crosslinking to fibrin, α2AP forms a new epitope that is unique to clots.

An antibody that exclusively inhibits α2AP crosslinked to fibrin can be used to target plasminogen activators to a clot as well as to amplify their thrombolytic effects. Since antiplasmin crosslinked to fibrin is present in small quantities and only at the clot surface, such an antibody is the ideal inhibitor: it prolongs the half-like of plasmin proximity to the clot while not interfering with the inactivation of circulating plasmin by soluble α2AP. As such it could not cause systemic thrombolysis. Such an agent can induce an ultra-specific α2AP deficiency at the site of the clot. In doing so, it could augment the normal clot lysis initiated by endogenous t-PA, and reproduce the spontaneous thrombolysis noted in studies of α2AP deficiency. If the antibody were given with a clot-specific agent such as t-PA, even more specific lysis would be obtained than has previously been seen. In addition, because of its combined specificity for the clot, and its capacity to simultaneously inhibit fibrin-crosslinked α2AP, this antibody would be extremely useful as a means of targeting plasminogen activators to the clot. Accordingly, the present invention provides antibodies which bind to and inhibit α2AP crosslinked to fibrin, but do not inhibit soluble α2AP.

E. Summnary

In summary, a substantial goal of therapies aimed at treating myocardial infarction involves limiting necrosis by permitting early reperfusion and by preventing reocclusion. At present, this goal is partially achieved through the administration of thrombolytic agents capable of dissolving the potentially life-threatening fibrin-platelet clots. The potential benefit of employing such agents is, however, significantly offset by their lack of fibrin specificity (as in the case of streptokinase and urokinase), or by their relatively short biological half-life caused by plasmin inhibitors (which may result in reformation of the fibrin clot, and the accompanying reocclusion of the affected blood vessels). Hence, a need exists for an improvement in thrombolytic therapy which specifically enhances clot lysis, while minimizing fibrinogen breakdown and preventing reocclusion of the affected coronary artery.

SUMMARY OF THE INVENTION

It is a general object of the invention to provide a method for treating myocardial infarction or a blood clot within a patient.

It is a specific object of the invention to provide a method for treating myocardial infarction or a blood clot within a patient comprising administering to the patient a therapeutically effective amount of an antibody or fragment thereof capable of binding α2-antiplasmin crosslinked to fibrin wherein the antibody does not inhibit plasma α2-antiplasmin.

It is another specific object of the invention to provide a method of treatment for myocardial infarction or blood clots within a patient which comprises co-administering to the patient:

(a) an antibody or fragment thereof capable of binding α2-antiplasmin crosslinked to fibrin in a therapeutically effective amount wherein the antibody does not inhibit plasma α2-antiplasmin; and (b) a thrombolytic agent in an amount sufficient to either (i) dissolve a fibrin-platelet clot or (ii) inhibit the formation of a fibrin-platelet clot.

It is a further specific object of the invention to provide a monoclonal antibody or fragment thereof wherein the antibody or fragment thereof is capable of binding α2-antiplasmin crosslinked to fibrin and does not inhibit plasma α2-antiplasmin.

It is another specific object of the invention to provide a kit useful for carrying out the above-described methods, comprising a carrier means being compartmentalized in close confinement to receive two or more container means therein, which comprises:

(1) a first container means containing a therapeutically effective amount of the above-described antibody or fragment thereof; and (2) a second container containing a therapeutically effective amount of a thrombolytic agent.

Further objects and advantages of the present invention will be clear from the description that follows.

BRIEF DESCRIPTION OF THE DRAWINGS

FIG. 2. Binding of α2AP-Fx monoclonal antibodies to fibrinogen.

FIG. 3. Clot lysis by α2AP-Fx monoclonal antibodies.

FIG. 4. Inhibition of soluble α2AP by α2AP-Fx monoclonal antibodies.

DETAILED DESCRIPTION OF THE INVENTION

Figure 1:
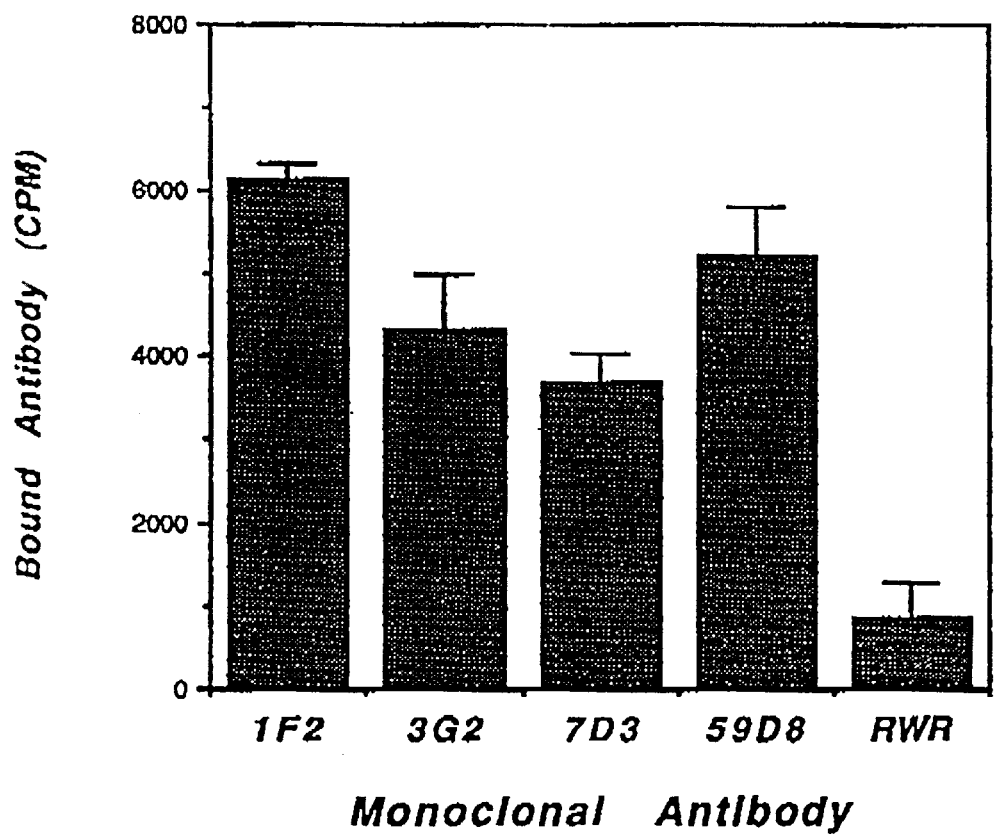
FIG. 1. Binding of monoclonal antibodies to clots in the presence of an excess of soluble α2-antiplasmin.

The present invention is directed to a method for treating myocardial infarction or a blood clot within a patient comprising administering to the patient a therapeutically effective amount of an antibody or fragment thereof capable of binding α2-antiplasmin crosslinked to fibrin wherein the antibody does not inhibit plasma α2-antiplasmin.

The present invention also involves a method of treatment for myocardial infarction or blood clots within a patient which comprises co-administering to the patient: (a) a therapeutically effective amount of an antibody or fragment thereof capable of binding α2-antiplasmin crosslinked to fibrin wherein the antibody does not inhibit plasm α2-antiplasmin; and (b) a thrombolytic agent in an amount sufficient to either (i) dissolve a fibrin-platelet clot or (ii) inhibit the formation of a fibrin-platelet clot.

Blood clots which may be treated according to the methods of the invention include, but are not limited to pulmonary thromboembolism, deep venous thrombosis, cerebral embolism, renal vein and peripheral arterial thrombosis, and the like.

Antibody fragments include F(ab')$_2$ or F(ab) molecules, as well as any fragment capable of binding to α2-antiplasmin crosslinked to fibrin wherein the antibody fragment does not inhibit plasma α2-antiplasmin. Preferably, the antibody or fragment thereof is substantially purified and/or isolated.

The antibodies or fragments thereof of the present invention can be monoclonal antibodies or fragments thereof. It is preferable to employ the F(ab')$_2$ fragment of such an antibody for this purpose, in order to minimize any immunological reaction caused by the Fc portion of the immunoglobulin. Procedures for preparing monoclonal antibodies are disclosed by Kaprowski, H. et al. (U.S. Pat. No. 4,172,124); and Kohler et al. (*Nature* 256:495–497 (1975)). More specifically, the preparation of monoclonal antibodies capable of preventing the inhibition of plasmin are taught by Mimuro, J. et al., *Blood* 69:446453 (1987).

Another method for obtaining the monoclonal antibodies of the present invention is to use peptide immunogens which mimic the unique crosslinked α2AP-Fx epitope. For example, it is possible to synthesize a peptide containing the α2AP-Fx crosslink as shown below:

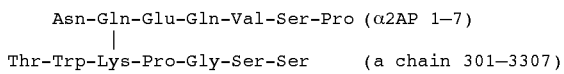

To synthesize this crosslinked sequence, the combined Boc and F-moc strategy would be used. A peptide that imitates the gamma-gamma chain crosslink of fibrin has been used successfully as an immunogen to generate antibodies that specifically recognize the gamma-gamma crosslink site in fibrin (Matsueda, G. R. et al., *FASEB J.* 2:A1411 (1988)). Once synthesized, the α2AP-fibrin crosslink peptide will be coupled to keyhole limpet hemocyanin. It will then be used as an immunogen. In a preferred embodiment, the antibody or fragment thereof is capable of binding a peptide comprising the α2AP-Fx crosslink as shown below:

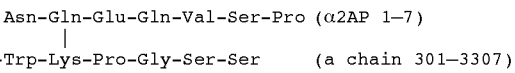

The invention also provides hybridomas which are capable of producing the above-described antibodies. A hybridoma is an immortalized cell line which is capable of secreting a specific monoclonal antibody.

The term "thrombolytic agent" is meant to refer to any agent capable of either dissolving a fibrin-platelet clot, or inhibiting the formation of such a clot. Examples of thrombolytic agents include streptokinase, prourokinase, urokinase, and tissue-type plasminogen activator. Use of t-PA for these purposes is especially preferred. Although natural t-PA may be employed, it is preferable to employ recombinant t-PA. The invention may additionally employ hybrids, physiologically active fragments or mutant forms of the above thrombolytic agents. The term "tissue-type plasminogen activator" as used herein is intended to include such hybrids, fragments and mutants, as well as both naturally derived and recombinantly derived tissue-type plasminogen activator.

By the term "co-administered", it is intended that each of the antibody or fragment thereof and thrombolytic agent will be administered during a time frame wherein the respective periods of pharmacological activity overlap. The two agents can be administered simultaneously or sequentially.

As stated, the methods of the invention comprise the administration of the antibody or fragment thereof alone or in combination with a thrombolytic agent. When administered alone the antibody may enhance in vivo thrombolysis by significantly augmenting clot lysis by endogenous plasminogen activators. Alternatively, the antibody or fragment thereof is administered with a thrombolytic agent. In this embodiment, the antibody or fragment thereof and the thrombolytic agent of the present invention are intended to be co-administered to the recipient. It is preferable to provide the antibody or fragment thereof to the patient prior to the administration of the thrombolytic agent. It is most preferable to provide the antibody or fragment thereof 45 minutes, preferably 30 minutes, prior to the administration of the thrombolytic agent.

When used alone, an amount of the antibody or fragment thereof capable of enhancing clot lysis when provided to a patient is a "therapeutically effective" amount. In order to enhance clot lysis and prevent clot reformation, it is desirable to provide between 3 to 100 nmole of antibody or fragment thereof per kilogram of patient weight, and most preferably between 3 to 6 nmole of antibody or fragment thereof per kilogram of patient weight. This dosage may be administered, in one embodiment, over a period of between 60 to 480 minutes, by continual intravenous infusion at a rate of 0.10–1.0 mg/kg min. Alternatively, it is possible to provide the antibody or fragment thereof in an intravenously injectable bolus at a dose of between 3 to 100 nmole/kg, and most preferably between 3 to 6 nmole (of antibody or fragment thereof) per kilogram of patient weight. If the antibody or fragment thereof is provided in this manner, a single bolus is sufficient to prevent potential clot reformation. The antibody or fragment thereof of the present invention may be dissolved in any physiologically tolerated liquid in order to prepare an injectable bolus. It is preferable to prepare such a bolus by dissolving the antibody or fragment thereof in normal saline.

When the antibody or fragment thereof is co-administered with a thrombolytic agent, it is desirable to provide between 3 to 100 nmole of antibody or fragment thereof per kilogram of patient weight, and most preferably between 3 to 6 nmole of antibody or fragment thereof per kilogram of patient weight. This dosage may be administered, in one embodiment, over a period of 60 to 480 minutes, by continuous intravenous infusion. Alternatively, it is possible to provide the antibody or fragment thereof in an intravenously injectable bolus at a dose of between 3 to 100 nmole/kg, more preferably 3 to 6 nmole/kg, and most preferably between 1 to 3 nmole/kg of patient weight. An amount of thrombolytic agent capable of causing such lysis is a "therapeutically effective" amount. The thrombolytic agent of the present invention is preferably provided at a dose of between 0.5 to 1.0 mg per kg of patient weight. In one embodiment, the thrombolytic agent is provided over a prolonged period (i.e., from about 180 to about 1440 minutes). In a preferred embodiment, the thrombolytic agent of the present invention is provided as an intravenously injected bolus containing between 0.5 to 1.0 mg/kg, and most preferably between 0.5 to 0.75 mg/kg. The thrombolytic agent of the present invention may be dissolved in any physiologically tolerated liquid in order to prepare an injectable bolus. It is, however, preferable to prepare such a bolus by dissolving the thrombolytic agent in normal saline.

A patient treated according to the preferred embodiment will, therefore, receive an intravenously injected bolus of the antibody or fragment thereof in combination with an intravenously injected bolus of the thrombolytic agent. This preferred treatment minimizes the amount of t-PA required for thrombolysis, thus reducing the extent of fibrinogen breakdown and lessening any tendency for general hemorrhage. Importantly, the use of the preferred treatment results in the dissolution of the occluding thrombus at a rate which greatly exceeds the rate of thrombus dissolution when either the antibody (or fragment thereof) or the thrombolytic agent is provided by infusion. Additionally, the risk of reocclusion is substantially reduced.

As would be apparent to one of ordinary skill in the art, the required dosage of the antibody (or fragment thereof) or thrombolytic agent will depend upon the severity of the condition of the patient, and upon such criteria as the patient's height, weight, sex, age, and medical history.

The antibody (or fragment thereof) or thrombolytic agent of the present invention can be formulated according to known methods to prepare pharmaceutically useful compositions, such as by admixture with a pharmaceutically acceptable carrier vehicle. Suitable vehicles and their formulation are described, for example, in *Remtington's Pharmaceutical Sciences* (16th Ed., Osol, A. (ed.), Mack, Easton Pa. (1980)). In order to form a pharmaceutically acceptable composition suitable for effective administration, such compositions will contain an effective amount of the antibody (or fragment thereof) or thrombolytic agent, either alone, or with a suitable amount of carrier vehicle.

Additional pharmaceutical methods may be employed to control the duration of action. Controlled release preparations may be achieved by the use of polymers to complex or absorb the antibody (or fragment thereof) or thrombolytic agents of the present invention. The controlled delivery may be exercised by selecting appropriate macromolecules (for example, polyesters, polyamino acids, polyvinyl pyrrolidone, ethylenevinylacetate, methylcellulose, carboxymethylcellulose, or protamine sulfate). The rate of drug release may also be controlled by altering the concentration of such macromolecules. Another possible method for controlling the duration of action comprises incorporating the therapeutic agents into particles of a polymeric substance such as polyesters, polyamino acids, hydrogels, poly(lactic acid) or ethylene vinylacetate copolymers. Alternatively, it is possible to entrap the therapeutic agents in microcapsules prepared, for example, by coacervation techniques or by interfacial polymerization, for example, by the use of hydroxymethylcellulose or gelatin-microcapsules or poly(methylmethacrylate) microcapsules, respectively, or in a colloid drug delivery system, for example, liposomes, albumin microspheres, microemulsions, nanoparticles, nanocapsules, or in macroemulsions. Such teachings are disclosed in *Remington's Pharmaceutical Sciences* (1980).

The antibody (or fragment thereof) or thrombolytic agent may be provided to a patient by means well known in the art. Such means of introduction include oral means, intranasal means, subcutaneous means, intramuscular means, intravenous means, intra-arterial means, or parenteral means. In the most preferred method of treatment for myocardial infarction, a patient is provided with a bolus (intravenously injected) containing between 0.5 to 1.0 mg/kg.

By virtue of their recognition of α2AP crosslinked to fibrin, the antibodies of the present invention will be thrombus-specific, and are useful for targeting plasminogen activators to the clot; the diagnostic detection of thrombi; inhibiting the reversible crosslinking of α2AP to fibrin and thus should secondarily increase thrombolysis; and these MAbs should also not interfere with the inactivation of plasmin by α2AP, and thus markedly amplify the effects of endogenous or administered plasminogen activators.

The present invention also provides a method of detecting the presence of a clot (more specifically, a fibrin-platelet clot) in a biological sample, comprising: (a) contacting the sample with the above-described antibody wherein the antibody is specific for an antigenic determinant characteristic of the clot, under conditions such that binding of the antibody to the antigenic determinant occurs, and (b) detecting the presence of the antibody bound to the antigenic determinant, the binding being related to the presence of a clot in the sample.

The present invention further provides a method of diagnosing the presence of a clot in a patient comprising administering to the patient a conjugate comprising: (a) the above-described antibody or fragment thereof, linked directly or indirectly to (b) a moiety capable of being detected by a source external to the patient, and detecting the presence of the detectable moiety.

The present invention is described in further detail in the following non-limiting examples.

EXAMPLE 1

Preparation of α2AP-Fx Immunogen

Typically 100 to 1000 ml of pooled plasma was clotted with 20 mM $CaCl_2$ and 100 units of thrombin overnight at 37° C. The clot was washed with TBSA containing 2 mM $CaCl_2$, 100 mM EACA and 1 mM iodoacetamide until the A280 was less than 0.03. Then 1 mg of thermolysin in 10 ml of 0.1 M Na Borate pH 7.2 with 2 mM $CaCl_2$ was added. The clot was incubated at 37° C. until it was visibly digested. Then it was centrifuged at 4000 rpm for 15 minutes and the supernatant was filtered through a 5 μM filter. Subsequently, it was incubated with polyclonal rabbit anti-α2AP agarose, or RWR agarose for 2 hours at room temperature. After washing with PBS with 0.5 M NaCl until the A280 was <0.02, the bound α2AP-Fx fragments were eluted with 0.2 M glycine pH 2.8 and neutralized with 1.0 M Tris, pH 8.0.

EXAMPLE 2

Generation of Monoclonal Antibodies

Mice were repeatedly immunized subcutaneously with approximately 50 μg of purified α2AP-Fx antigen. Somatic cell fusion was performed as described (Reed et al. *Proc. Natl. Acad. Sci. USA* 87:1114–1118 (1990)). Hybridomas showing binding were then rescreened for their ability to bind to α2AP crosslinked to fibrin in washed clots in the presence of a 10-fold excess of plasma supernatant containing soluble antiplasmin as an inhibitor. After washing the clots and removing the plasma supernatant, bound antibody was detected by the addition of $^{125}$I-goat antimouse antibody. MAbs showing no significant inhibition by plasma were selected for further study. FIG. 1 demonstrates that these MAbs (1F2, 3G2, 7D3) bound to clots at a level comparable to that of a specific antifibrin antibody (59D8) and to a much greater extent than did the antibody to both soluble and fibrin crosslinked α2-antiplasmin (RWR). Under the terms of the Budapest Treaty on the International Recognition of the Deposit of Micro-organisms for the Purposes of Patent Procedure, a hybridoma cell line producing monoclonal antibody 1F2 was deposited with the following International Depository Authority: American Type Culture Collection, now located at 10801 University Blvd., Manassas, Va. 20110–2209 USA. The deposit was made on Jul. 11, 1996, and given the accession number ATCC HB-12149. Under the terms of the Budapest Treaty on the International Recognition of the Deposit of Micro-organisms for the Purposes of Patent Procedure, a hybridoma cell line producing monoclonal antibody 3G2 was also deposited with the following International Depository Authority: American Type Culture Collection, now located at 10801 University Blvd., Manassas, Va. 20110–2209 USA. The deposit was made on Jul. 11, 1996, and given the accession number ATCC HB-12148.

To verify that the MAbs obtained did not bind to fibrinogen solid phase binding experiments were performed (FIG. 2). Wells of a microtiter plate were coated with purified fibrinogen or a control antigen. The hybridoma supernatant was then incubated in these wells for one hour. After washing the amount of bound antibody was determined by the addition of $^{125}$I-goat antimouse antibody. The specific binding of these antibodies to fibrinogen was compared to a positive control (antifibrinogen MAb 4A5, and antifibrin 59D8) and a negative control MAb (RWR). These MAbs appeared to show little or no significant binding to this fibrinogen preparation.

Clot lysis assays were performed to determine whether these MAbs could inhibit α2AP crosslinked to fibrin. Plasma (100 μl) was clotted with trace amounts of radiolabelled fibrinogen. Then hybridoma supernatants (in triplicate) were added to each clot with 1 unit of t-PA. The clots were incubated overnight and the amount of lysis was compared to RWR (positive control) and buffer alone (negative control). Compared to the negative control, hybridomas 1F2, 4H6 and 3G2 accelerated clot lysis at levels which were comparable to the other MAb RWR (FIG. 3).

Given that the MAbs appeared to enhance clot lysis by inhibiting α2AP-Fx, it was next tested whether they could inhibit soluble α2AP in plasma. A standard α2AP assay was performed essentially as previously described using the Stachrom kit (Reed et al., *Circulation* 82:164–168 (1990)), i.e., residual α2-antiplasmin activity was measured by a chromogenic substrate assay kit from Stachrom (Asnières, France), except that hybridoma culture supernatants were added as inhibitors. FIG. 4 shows that RWR significantly inhibited the α2AP in plasma but 3G2 and 1F2 had no significant inhibitory effect on soluble α2AP.

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. A monoclonal antibody or fragment thereof wherein said antibody or fragment thereof is specific to an epitope formed by the crosslinking of α2-antiplasmin to fibrin and inhibits α2-antiplasmin crosslinked to fibrin so as to increase endogenous fibrinolysis but does not interfere with the inactivation of circulating plasmin by soluble α2-antiplasmin.

2. A kit useful for carrying out a method of treatment for myocardial infarction or blood clots within a patient which comprises co-administering to said patient:
   (a) an antibody or fragment thereof which is specific to an epitope formed by the crosslinking of α2-antiplasmin to fibrin and inhibits α2-antiplasmin crosslinked to fibrin so as to increase endogenous fibrinolysis but does not interfere with the inactivation of circulating plasmin by soluble α2-antiplasmin, in a therapeutically effective amount; and
   (b) a thrombolytic agent in an amount sufficient to either (i) dissolve a fibrin or fibrin-platelet clot or (ii) inhibit the formation of a fibrin or fibrin-platelet clot, comprising a carrier means being compartmentalized in close confinement to receive two or more container means therein, which comprises:
      (1) a first container means containing a therapeutically effective amount of said antibody or fragment thereof (a); and
      (2) a second container containing a therapeutically effective amount of said thrombolytic agent (b).

3. The kit according to claim 2, wherein said thrombolytic agent is selected from the group consisting of streptokinase, prourokinase, urokinase, staphylokinase and tissue-type plasminogen activator.

4. The kit according to claim 3, wherein said thrombolytic agent is tissue-type plasminogen activator.

5. The monoclonal antibody or fragment thereof of claim 1, wherein said antibody or fragment thereof is generated by immunizing an animal with α2-antiplasmin crosslinked to fibrin.

6. The kit of claim 2, wherein said antibody or fragment thereof (a) is generated by immunizing an animal with α2-antiplasmin crosslinked to fibrin.

7. A monoclonal antibody or fragment thereof wherein said antibody or fragment thereof is specific to an epitope formed by the crosslinking of α2-antiplasmin to fibrin and inhibits α2-antiplasmin crosslinked to fibrin so as to increase endogenous fibrinolysis, and wherein the mean inhibition of soluble or plasma α2-antiplasmin by said antibody or fragment thereof, as measured using a chromogenic substrate assay, is about equal to or less than that of monoclonal antibody 1F2 (ATCC HB-12149).

8. The monoclonal antibody or fragment thereof of claim 7 wherein said antibody or fragment thereof is generated by immunizing an animal with α2-antiplasmin crosslinked to fibrin.

9. The kit of claim 2, wherein the mean inhibition of soluble or plasma α2-antiplasmin by said antibody or fragment thereof (a), as measured using a chromogenic substrate assay, is about equal to or less than that of monoclonal antibody 1F2 (ATCC HB-12149).

10. The kit of claim 9, wherein said antibody or fragment thereof (a) is generated by immunizing an animal with α2-antiplasmin crosslinked to fibrin.

* * * * *